_United States Patent_ [19]

Tomasi et al.

[11] Patent Number: 4,732,863

[45] Date of Patent: Mar. 22, 1988

[54] PEG-MODIFIED ANTIBODY WITH REDUCED AFFINITY FOR CELL SURFACE FC RECEPTORS

[75] Inventors: Thomas B. Tomasi, Corrales; William L. Anderson, Albuquerque, both of N. Mex.

[73] Assignee: University of New Mexico, Albuquerque, N. Mex.

[21] Appl. No.: 687,811

[22] Filed: Dec. 31, 1984

[51] Int. Cl.⁴ .................. G01N 33/53; G01N 33/532; G01N 33/574; G01N 33/577
[52] U.S. Cl. ...................................... 436/547; 424/1.1; 424/9; 436/548; 436/804; 436/813; 530/387
[58] Field of Search ............... 436/547, 548, 804, 813; 260/112 R, 112 B; 435/181, 188; 530/387; 424/1.1, 9

[56] References Cited

U.S. PATENT DOCUMENTS

| | | | |
|---|---|---|---|
| 4,384,993 | 5/1983 | Sato et al. | 424/85 |
| 4,407,965 | 10/1983 | Yanaihara | 436/547 |
| 4,427,653 | 1/1984 | Springer | 424/85 |
| 4,495,285 | 1/1985 | Shimizu | 435/215 |

FOREIGN PATENT DOCUMENTS 2606118 8/1976 Fed. Rep. of Germany .
2856939 7/1980 Fed. Rep. of Germany .

OTHER PUBLICATIONS

Boccu, E. et al., Z. Naturforsch., Section C, Biosci, vol. 38c, No. 1/2, 94–99 (1983).
Chemical Abstracts, 98:15249k (1983).
Ling, T. G. I. et al., J. Immunol. Meth., 59, 327–337 (1983).
Mellman et al, "Purification of a Functional Mouse Fc Receptor Through the Use of a Monoclonal Antibody", J. Exp. Med., vol. 152, Oct. 1980, pp. 1048–1049.

_Primary Examiner_—Sidney Marantz
_Attorney, Agent, or Firm_—Charles W. Fallow; Martin P. Hoffman; Mitchell B. Wasson

[57] ABSTRACT

PEG-modified protein molecules characterized by reduced immunogenicity are prepared by covalent modification of the protein with PEG employing an active ester intermediate. Antibodies so modified exhibit decreased binding capacity for Fc cell surface receptors, are non-toxic and retain full antigen binding activity, and are consequently useful in a variety of immunologically-based diagnostic and therapeutic procedures.

22 Claims, 9 Drawing Figures

PEG-MODIFIED ANTIBODY WITH REDUCED AFFINITY FOR CELL SURFACE FC RECEPTORS

GOVERNMENT RIGHTS UNDER 35 U.S.C. 202

Research leading to this invention was, in part, funded by the National Cancer Institute, Grant Number NCIRO1-CA37063, and rights accruing under any patent granted herein may be affected accordingly.

BACKGROUND OF THE INVENTION

1. Field of the Invention

Diagnostic and therapeutic procedures of the type dependent upon immunoreaction of antibody with a target tissue are frequently hampered by both the immunogenicity of the reagent in clinical applications and binding to cell surface Fc receptors. Immune response to antibodies and other foreign proteins, characterized by both allergic phenomena and inactivation of the protein, must be countered by treatment of the protein to obviate stimulation of the host immune system while retaining desirable protein biologic activity. In addition, it is desirable to increase antibody specificity by reduction or elimination of Fc binding to cell surface receptors.

2. Statement of Related Art

A variety of protein-modifying procedures has been employed to decrease immunogenicity of foreign proteins. In particular, suppression of human immunologic response to foreign antibodies without destruction of antibody activity has been previously accomplished by enzymatic digestion of the antibody to cleave the Fc fragment of the molecule. The product fragments retain binding capacity for antigen and can be coupled with a variety of chemicals to provide complexes of low immunogenicity. Protease digestion of antibodies is, however, a slow process with low yields, requiring separation of the product fragments.

A more attractive approach has been the proposed chemical modification of antibodies to provide products having high antigen binding capacity, low immunogenicity, and substantially no toxicity. Such proposed modifications have been broadly based on the known immunoinhibitory effect of hydrophilic polymers such as polyethylene glycol (PEG) and polyvinyl alcohol (PVA) on therapeutically useful enzymes, cf: *J. Biol. Chem.* 252: 3578–3586 (1977); *Biochim. Biophys. Acta* 660: 293–298 (1981); *Clin. Exp. Immunol.* 46: 649–652 (1981); *Biochim. Biophys. Acta* 578: 47–53 (1979); *Int. Arch. Allergy Appl. Immunol.* 56: 159–170 (1978); *J. Immunol.* 126: 407–413 (1981); and *Int. Arch. Allergy Appl. Immunol.* 63: 1–13 (1980). The reported modification procedures have not been generally applicable to antibodies, however. In an exemplary investigation, reported in *Radioimmunoimaging and Radioimmunotherapy*, Elsevier Science Publishing Co. New York, N.Y., 1983, a PEG 6000 derivative of rabbit antihuman serum albumin was prepared employing a cyanuric chloride coupling procedure successfully employed in the modification of albumin with PEG (*J. Biol. Chem.* 252: 3578–3581, 1977). While the product exhibited reduced immunogenicity, loss of avidity for antigen was unacceptable (nearly 70% reduction in binding capacity). A similar result was obtained in a related study *J. Immunol. Methods*, 59: 327 (1983), wherein it was concluded that PEG-modification of Ig mediated with cyanuric chloride destroyed antibody activity.

SUMMARY OF THE INVENTION

The invention comprises a polyethylene glycol-protein derivative, and a method for preparing the derivative in excellent yields comprising covalently modifying the protein with polyethylene glycol (PEG) employing an active ester intermediate. Derivatized antibodies are characterized by retained antigen binding activity, low binding capacity for cell surface Fc receptors, reduced immunogenicity, good storage stability, and non-toxicity, and are useful in conventional immunological techniques such as tumor imaging, chemotherapy, radiotherapy, and immunohistochemical procedures. It is contemplated that a broad range of diagnostic and therapeutic proteins, including monoclonal antibodies and enzymes, is modifiable by the process of the invention to provide modified proteins having reduced immunogenicity and low non-specific biological activity.

DETAILED DESCRIPTION OF THE INVENTION

Figure 1:
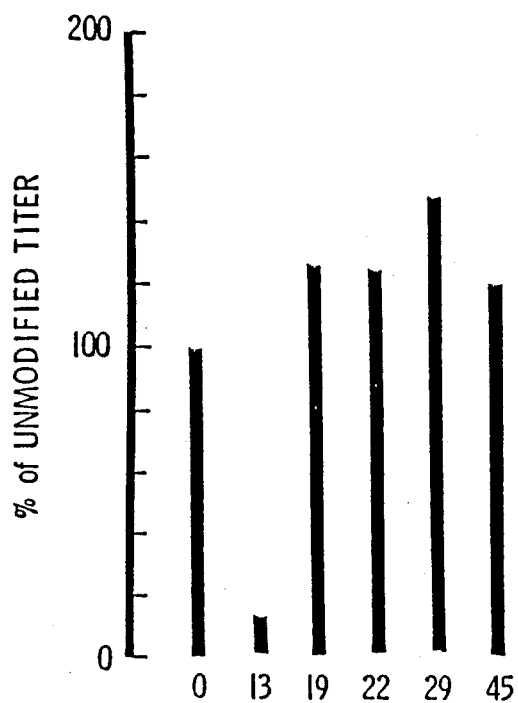
FIG. 1 represents SDS-disc gel electrophoresis of rabbit anti-conalbumin modified with the N-hydroxysuccinimide ester of mPEG succinate. The gels were stained with coomassie blue and were scanned in a densitometer at 600 nm. The numbers in the figure correspond to the percentage of mPEG-modified amino groups.

According to the invention, immunogenicity of foreign protein, especially antibody, is reduced or eliminated by covalent modification of the protein with polyethylene glycol (PEG), employing a PEG active ester intermediate. In contrast to known prior art modifications, PEG modification of antibodies according to the process of the invention provides a derivative which retains avidity for antigen, while exhibiting reduced immunogenicity. A particular advantage of the present invention is that a significant reduction in non-specific binding occurs, which is believed to be attributable to inactivation of the Fc portion of the antibody molecule. The process thus substantially eliminates binding of the antibody to cell surface Fc receptors and promotes antibody concentration targeted tissue in applications such as tumor imaging and immunohistochemical techniques.

Particular PEG polymers useful in the process of the invention comprise substituted or unsubstituted PEG polymers having molecular weights of from about 1000 to 5000, which are themselves poor immunogens, and which can be coupled to protein using an active ester intermediate; the resulting modified protein must be biologically active and substantially non-toxic and non-immunogenic. Monomethoxypolyethylene glycol (mPEG) satisfies these criteria, and is an especially suitable modifier, particularly for antibody. Covalent mPEG modification of antibody molecule, using the present active ester approach, is accomplished with full retention of binding activity, and yields very predictable and reproducible modifications.

Protein modification according to the present invention occurs through covalent attachment of PEG to TNBS-available (trinitrobenzene sulfonic acid-available) amino groups on the protein molecule. The immunogenicity of PEG-modified derivatives varies with the degree of modification, which is readily controlled by an appropriate selection of ratio of active ester to protein. At optimal ranges of derivatization (with typically about 10-20% of the available amino groups modified), most antibodies will not give rise to an immune response following exposure to the modified antibody in usual diagnostic and therapeutic amounts. At higher or lower degrees of modification, immunogenicity may be restored or even enhanced, depending upon the protein and the PEG modifier employed. Generally, immunoglobulin molecules with between 13-18% of the amino groups modified with mPEG lack detectable immunogenicity; however, at either a lower or higher degree of modification, the mPEG-antibody complex may induce an immune response to the unmodified molecule and in many cases an enhancement of the antibody response is observed. Antibody-mPEG derivatives of the present process retain full antigen binding activity with up to 35% of amino groups modified; since it has proved difficult to modify more than about 35% of available amino groups with mPEG using even a large excess of active ester, modification with mPEG is advantageously self-limiting in this respect. It is contemplated that most protein-mPEG derivatives having acceptably reduced immunogenicity will also retain effective antigen binding activity under the desired process conditions. It is noted that since the modified preparations described herein contain a distribution of molecules, the degrees of modification mentioned are an average of this distribution. It is possible that the ranges are dependent upon the degree of purification, and, in particular, that acceptably reduced immunogenicity may be obtainable over a broader range of modification with increased purity of starting materials.

PEG is covalently attached to the protein molecule in accordance with the invention as follows:

PEG + carboxylating agent→PEG-COOH             (1)

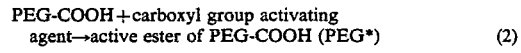
PEG-COOH + carboxyl group activating
   agent→active ester of PEG-COOH (PEG*)       (2)

Protein + PEG*→Protein-PEG                     (3)

As summarized in these equations, PEG is carboxylated, and the purified product (PEG-COOH) esterified with a suitable carboxyl activating agent to form the active ester PEG*. This active ester intermediate is then coupled to the protein molecule, with loss of the activating moiety. As previously noted, the modification yields a distribution of protein molecules, variously modified with PEG; the product may more accurately be represented as Protein-(PEG)$_x$, wherein x is the number of PEG groups on the protein molecule. The number of PEG groups x will vary according to the number of reactive amino groups present on the protein molecule. If an unpurified reaction product is employed, it is important that the amount of unsubstituted protein (x=0) be low, to avoid the possibility of inducing an immune response with the naked protein molecule.

Carboxylation of PEG to PEG-COOH and activation to the active ester intermediate PEG* is accomplished by any of several methods well-known in the art including methods employing carboxylating agents such as succinic anhydride, or classic textbook methods such as oxidation or the Williamson ether synthesis using chloroacetic acid. In a particularly useful embodiment, the selected PEG species is first succinylated with succinic anhydride to form PEG-COOH in step (1) of the reaction; PEG-COOH (succinylated) is then esterified with N-hydroxysuccinimide to form the active ester PEG* in step (2) of the reaction. The N-hydroxysuccinimide active ester is then reacted with the desired protein to form the PEG-Protein conjugate in step (3), with accompanying loss of the esterifying moiety. Carboxyl-activating agents of the type useful for activating PEG-COOH are well-known in the art; in addition to N-hydroxysuccinimide, trinitrophenol is exemplary. In contrast to known prior art methods such as those discussed supra for coupling PEG to protein, the process of the present invention provides an active, non-toxic product which retains biologic specificity but which has substantially lost non-specific reactivity.

The process of the present invention is applicable to a broad range of proteins to reduce the immunogenicity thereof when administered to a mammal, especially a human. While the process is particularly useful in reducing the immunogenicity of heterologous species proteins, the process is also applicable to homologous species proteins. Antibodies are proteins of particular interest, as by the process of the invention, the specificity and avidity of the antibody molecules is retained, while non-specific binding of antibody molecules to cellular Fc receptor and rapid clearance of the antibody from the circulation is obviated. Drugs, toxins, fluorescents, radionuclides, or other active moieties may readily be attached to the modified antibody molecule via the PEG substituent according to principles understood by those skilled in the art for delivery to selected tissue, especially to tumor tissue for diagnosis or therapy. Owing to the decreased non-specific activity of complexes comprising active moieties conjugated with PEG-modified antibody or other protein, premature dissociation of the complex is avoided, and highly selective delivery is achieved.

Monoclonal antibodies modified according to the invention also have increased with the present clinical use of unmodified MAbs of murine origin is the immune response of the host to the foreign protein, which both inactivates the MAb and has potential for the development of allergic reactions or serum sickness. The clinical use of human monoclonal antibodies may partially obviate such an immune response; however, even human MAbs carry allotypic and idiotypic antigenic sites which can stimulate the response. In addition, treatment with intact human MAb with an active moiety attached, may be equivalent to immunizing with a hapten-conjugated protein which could provoke an antihapten response. Modification of both human and animal MAbs according to the invention is thus particularly contemplated, in eliminating all these immune responses.

The modified antibodies of the invention are also useful in known tissue and cell staining procedures as substitutes for intact antibody to avoid non-specific staining owing to interaction between cellular Fc receptors and the Fc portion of the antibody. Other proteins modifiable according to the invention include enzymes, especially enzymes clinically useful in replacement therapy. Generally, the invention is applicable to proteins employed both in vitro and in vivo, wherein immunological procedures are hampered by immunogenicity of the protein and/or non-specific tissue binding.

The following Examples illustrate the practice of the invention:

EXAMPLES

MATERIALS AND METHODS

Preparation of Anti-Conalbumin Antibody

Rabbit anti-conalbumin antisera, was prepared by emulsifying hen egg conalbumin (Sigma, St. Louis, MO), dissolved in PBS with complete Freund's adjuvant (Gibco Laboratories, Grand Island, NY) at a final conalbumin concentration of 1.0 mg/ml. Rabbits were immunized in the footpads with a 1.0 ml aliquot of the emulsion and boosted subcutaneously 12–14 days later with 1 mg emulsified antigen. Blood samples from the immunized rabbits were routinely monitored for antibody content by Ouchterlony analysis. Only high titer, late course, antisera was used for the remaining experiments.

The anti-conalbumin antibody was isolated from the rabbit antisera by affinity chromatography on a CM-Biogel A (Bio-Rad Laboratories, Richmond, CA) column which was coupled to conalbumin using the water soluble carbodimide procedure (BioRad Lab. Chem. Div., Tech. Bul. 1075, Richmond CA, 1980). In brief, antisera was applied to the affinity column and the column was washed with 0.5M sodium thiocyanate and the resulting antibody was simultaneously desalted and concentrated using a Micro Pro di Con apparatus, (Bio Moleculare Dynamics, Beaverton, OR). The purified antibody was stored sterile at 4 degrees.

Measurement of Anti-Conalbumin Activity

Antigen binding activity of the affinity purified and chemically modified antibodies was determined by evaluating their ability to competitively inhibit the binding of a rabbit anti-conalbumin-alkaline phosphatase conjugate to conalbumin-coated microelisa plates (Vangard, Neptune, NJ). The enzyme linked antibody for this assay was prepared by a modification of the method described by Avermeas (Immuno. Chem. 6: 43, 1969) and to assure maximum sensitivity was titrated on the antigen coated plates prior to use in the assay. The conalbumin coated microelisa plates were prepared by diluting conalbumin to 10 μg/ml in 0.05M NaHCO$_3$, pH 9.6 and incubating for 18 hours at room temperature. Equal volumes of antibody and enzyme conjugate, at the proper dilution, were then incubated in the antigen coated plates with constant mixing for 2–5 hours at room temperature. Following washing of the plates with H$_2$O a 300 ml aliquot of p-nitrophenyl phosphate, 0.25 mg/ml, in 0.1N Tris-Cl, pH 10 was added to each well and, after an appropriate incubation, the absorbance at 410 nm and 650 m was read using a dynatech microelisa reader (Dynatech, Alexandria, VA). In all tests modified antibody was assayed simultaneously with a standard curve of unmodified affinity purified antibody and the data are expressed as relative mg antibody/mg protein. In this binding assay unmodified affinity purified antibody is defined as having a value of 1 mg antibody/mg protein. Chemical modifications with either block antigen binding or denature the antibody are characterized by a decrease in this number.

Characterization of Modified Antibody

Three different measurements were used to characterize the modified antibody. Protein concentration was determined both by optical density measurements at 280 nm, assuming an E % 280 nm=14 (*Methods Immunol. Immunochem.* 2: 343, 1968) and by using the dye binding assay (*Analyt. Biochem.* 72: 248, 1976) with a standard curve of rabbit gamma globulin. The concentration of the standard was evaluated by direct Nesslerization of a Kjeldahl digest (*Stanford Med. Bull.* 6: 97, 1948). Protein amino groups were determined by TNBS titrations as described by Habeed (*Analyt. Biochem.* 14: 328, 1966). The extent of PEG modification was also evaluated by measuring an increase in protein size. For this measurement protein size was evaluated using a 6% discontinuous SDS electrophoretic gel system. However, SDS gel size estimates of polymer modified immunoglobulin that are based on a standard curve of globular proteins will contain large errors. Therefore results are reported showing migration distance without the accompanying protein standards.

Determination of Immunogenicity

Immunogenicity of rabbit antibody and its PEG-modified derivatives were determined by measuring the antibody response of Swiss mice to an intraperitoneal injection of 50 g of the antigen (rabbit antibody) in PBS. The mouse antibody response was determined using a two step enzyme linked assay. In brief, several two-fold dilutions of mouse sera were incubated on a rabbit immunoglobulin coated microelisa plate for 2-5 hours. After extensive washing the plate was incubated with a rabbit anti-mouse alkaline phosphatase conjugate for an additional 2-5 hours. Following this second incubation, unbound conjugate was removed by extensive washing with H O and the wells were refilled with 300 ml of p-nitrophenyl phosphate, 0.25 mg/ml in 0.1N Tris-Cl, pH10. After a two-hour incubation period, the absorbance at 410 nm and 630 nm was measured as described previously. In this system antibody titer is defined as the greatest dilution giving an absorbance reading significantly above prebleed levels.

Chemical Modifications

Two different approaches were used to modify antibody with mPEG. Monomethoxypolyethylene glycol (av MW=5000) (Aldrich, Milwaukee, WI) was coupled to antibody using the cyanuric chloride (Eastman Chemical Co., Rochester, NY) procedure described in Abuchewski (*J. Biol. Chem.* 252: 3578, 1977). In addition, mPEG was also coupled to antibody using an active ester intermediate. To prepare this derivative mPEG was succinylated using an excess of succinic anhydride (Aldrich) in dry pyridine. The pyridine was removed by a combination of flash evaporation and lyophilization and the contaminating succinic acid was removed by dialysis. Purified mPEG succinate was lyophilized and dried in methylene chloride over molecular sieve 4A (Matheson Coleman & Bell, Norwood, OH). The mPEG succinate was then esterified in an equal molar mixture of DCC (Aldrich) and N hydroxysuccinimide (Aldrich) and the resulting N-hydroxysuccinimide ester was recovered by petroleum ether precipitation. The N-hydroxy-succinimide ester of mPEG succinate was purified by repeated recrystallization out of benzene with petroleum ether and was then dissolved in dry DMF and added with rapid mixing to a solution of antibody to be modified in 0.7M, NaHCO$_3$ pH 9.6. The extent of modification was controlled by varying the active ester to antibody ratio. The resulting mPEG modified antibody was purified by exhaustive dialysis against PBS.

Modification of Protein with FITC

Samples of conalbumin (Sigma Chemical Co., St. Louis, MO) and affinity purified rabbit anti-mouse immunoglobulin were fluorescein-labeled with FITC using the method of Goding (*J. Immunol. Meth.* 13: 215, 1976). Only protein samples with between 2 and 4 moles of fluorescein incorporated per mole of protein were used for further studies.

Polyethylene Glycol Modification

Affinity purified rabbit antibody was modified with polyethylene glycol using the N-hydroxysuccinimide ester of monomethoxypolyethylene glycol succinate (average molecular weight=5000). For each modified preparation the extent of the modification was established by both TNBS amino group analysis (*Analyt. Biochem.* 14: 328, 1966) and by nonreducing SDS-gel electrophoresis on 6% polyacrylamide gels (*Nature* 227: 680, 1970).

Evaluation of Cell Surface Binding

To evaluate binding of immune complexes of antibody preparations to cell surfaces, an aliquot of $1 \times 10^6$ cells was incubated with the test agent in PBS at 0 degrees for 30 minutes. Following this initial incubation, nonbound material was removed by washing the cells three times with PBS at 0 degrees. The final cell pellet was resuspended in 1 ml of PBS and the cell population analyzed for fluorescence using a fluorescent activated cell sorter (Becton Dickinson, Sunnyvale, CA). In each analysis greater than 1000 cells were counted. The cells were also examined by fluorescence microscopy to insure that cell surface fluorescence was being investigated. Two different populations of cells were used for these experiments. Splenocytes were obtained from Swiss mice (Sprague-Dawley, Madison, WI) and the contaminating erythrocytes were analysed using the ammonium chloride technique (Mishell et al, Preparation of Mouse Cell Suspensions in Selected Methods of Cellular Immunology [B. Mishell and S. Shiigi, eds.] W. H. Freeman and Col., San Francisco, p. 23, 1980).

Cell Lines

The murine macrophage line P3888.D1 was grown in the laboratory from a strain initially acquired from the American Type Tissue Collection, Bethesda, Md.

EXAMPLE I

Effect of mPEG modifications on antibody activity

The effect of mPEG modifications, using cyanuric chloride and active ester coupling procedures on antibody activity is reported in Table I and II. It is evident from these results that even at low modifications there is a significant decrease in antibody binding activity with cyanuric chloride. Experiments varying the rate and form of activated PEG along with experiments varying the reaction time and temperature did not significantly improve the recovery of active antibody. In contrast, the use of active ester to modify antibody with PEG results in no detectable loss in antibody titer or antibody activity.

TABLE I

Antigen Binding Activity of Rabbit Anti-Conalbumin Modified with mPEG using the Cyanuric Chloride Procedure

| % Lysine Modification | mg Antibody/mg Protein | % Loss of Ab Activity |
|---|---|---|
| 0 | 1.00 | 0 |
| 4 | 0.50 | 50 |
| 14 | 0.15 | 85 |
| 35 | 0.06 | 94 |

TABLE II

Antigen Binding Activity of Rabbit Anti-Conalbumin Modified with mPEG using the N—Hydroxy-Succinimide Ester of mPEG Succinate

| % Lysine Modification | mg Antibody/mg Protein | % Loss of Ab Activity |
|---|---|---|
| 0 | 1.0 | 0 |
| 8 | 1.0 | 0 |
| 12 | 1.0 | 0 |
| 18 | 1.0 | 0 |
| 22 | 1.0 | 0 |
| 30 | 1.0 | 0 |

EXAMPLE II

Effectiveness of modification of antibody of Example I with mPEG according to the invention To verify that antibody was significantly modified by this procedure, all mPEG-modified antibody preparations were analyzed by SDS gel electrophoresis. An example of one series of derivatives is shown in FIG. 1. Results from this experiment clearly show that most or all molecules in the population are modified and that the apparent molecular weight increases greatly following the modification. It should be noted however that the modified antibodies tested are a distribution of molecules each containing different number of PEG molecules per antibody. The reported % modification is then an average of this distribution.

EXAMPLE III

Immunogenicity of rabbit anti-conalbumin modified according to the invention

Figure 2:
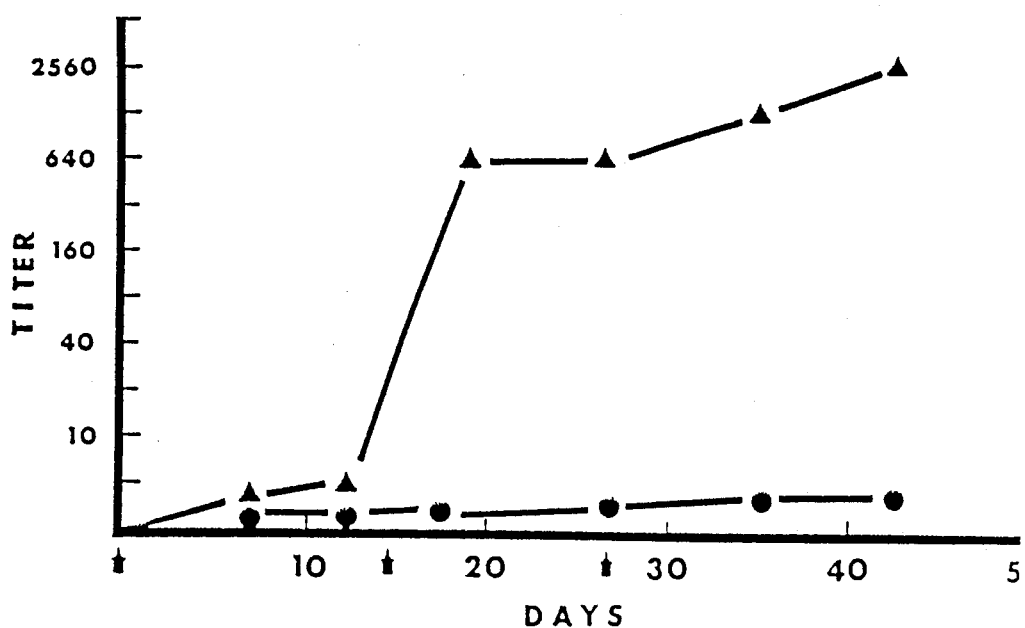
FIG. 2 represents immunogenicity of 50 μg rabbit anti-CALB given up to Ha/ICR mice was evaluated using EIA titrations with a rabbit anti-mouse IgG-alkaline phosphatase reagent as the second step. Time of immunization is indicated with the arrow. The anti-rabbit IgG response elicited by unmodified rabbit anti-CALB is shown with the triangle. The response elicited PEG-modified (18% of amino groups) is shown by the circles.
Figure 3:
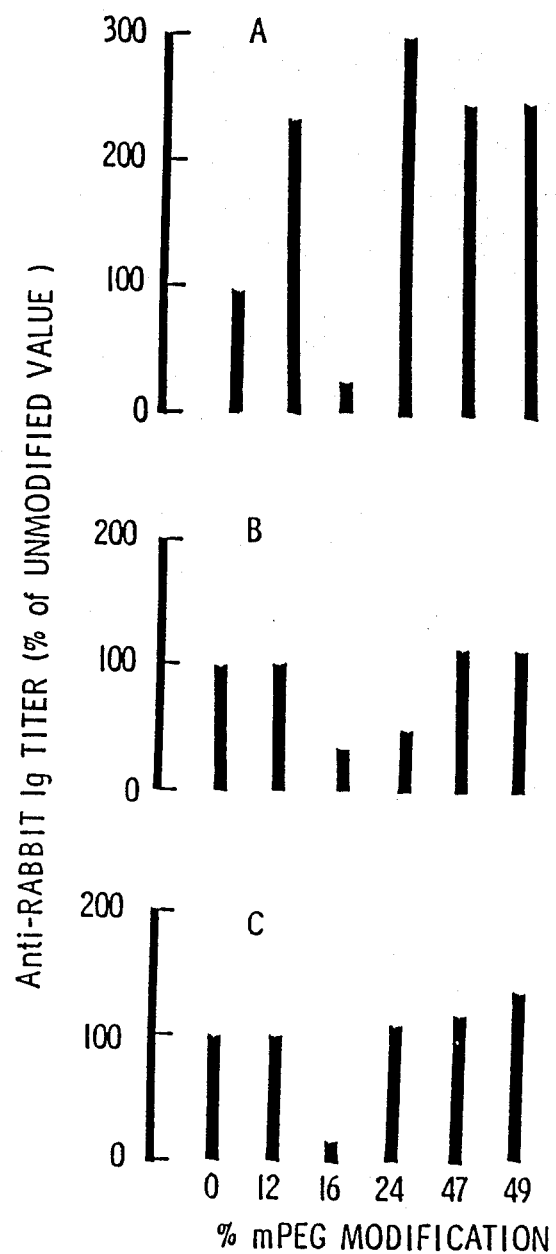
FIG. 3 represents effect of mPEG-modification on the immunogenicity, of rabbit anti-conalbumin. Swiss mice were immunized with 50 μg of antigen in PBS and the antibody response was evaluated using an enzyme immunoassay. Panel A depicts antibody titer 12 days following the primary immunization; Panel B, antibody titer 18 days following the primary immunization and three days following the secondary immunization; and Panel C, the antibody titer 35 days following the primary immunization and 9 days following the tertiary immunization.

The immunogenicity in Swiss mice of mPEG modified rabbit anti-conalbumin (18% of amino groups modified) (active ester coupling agent) compared to the immunogenicity of unmodified rabbit antibody is shown in FIG. 2. This figure clearly demonstrates that under the proper modification conditions immunogenicity of rabbit antibody can be substantially eliminated. The modified antibody tested in this experiment retained complete antigen binding activity. The effect of variation in mPEG content of modified rabbit antibody on immunogenicity in the mouse is shown in FIG. 3. Similar results are seen after primary, secondary or tertiary immunizations and these results are essentially identical to those found for the rabbit antibody prepared by the cyanuric chloride procedure (Example I). It is emphasized that, in contrast to the derivatives prepared with cyanuric chloride, all rabbit antibodies tested in this experiment maintained complete antibody activity. Similar results were obtained with anti-human serum albumin antibody.

EXAMPLE IV

Evaluation of mouse immune response to rabbit antibody

Figure 4:
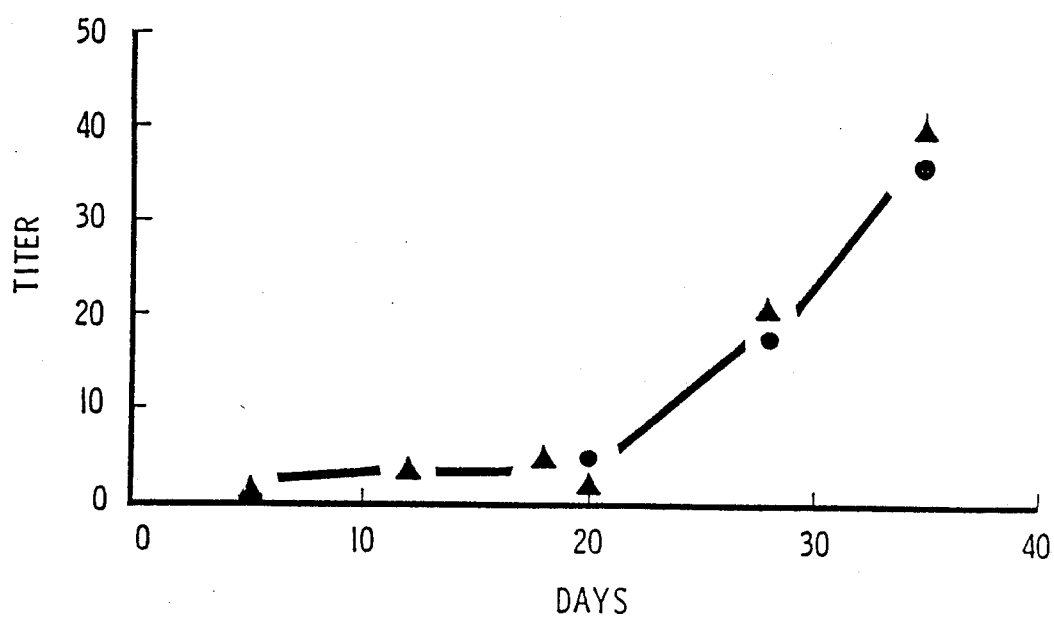
FIG. 4 represents effect of treatment with mPEG modified rabbit anti-conalbumin has on the antibody response to unmodified rabbit anti-conalbumin. Swiss mice were either untreated (●) or immunized with 50 μg of nonimmunogenic mPEG (▲) 5 and 20 days prior to the immunization with 50 μg of unmodified rabbit anti-conalbumin (Day 20). Mouse anti-rabbit immunoglobulin titer was determined using an enzyme-linked assay.

A. To eliminate the possibility that the lack of a response to mPEG-modified antibody was due to the induction of tolerance, Swiss mice were immunized twice with 50 μg of nonimmunogenic mPEG-modified antibody. After determining that the immunized animals exhibited no response to rabbit antibody modified with mPEG, according to the present invention, the immune animals and native control animals were challenged with a 50 μg aliquot of unmodified rabbit antibody. Twelve days following this challenge the mouse anti-rabbit immunoglobulin was determined. The results of this experiment, shown in FIG. 4, demonstrate no differences in the response to two test groups of animals to rabbit antibody, suggesting that the mPEG-modified antibody neither tolerized nor primed the experimental animals.

B. The hyperresponsiveness induced by some of the mPEG-modified rabbit antibodies in A, supra, was investigated by evaluating the adjuvant properties of PEG. Swiss mice were immunized with 50 μg of rabbit immunoglobulin in the presence of varying PEG concentrations up to 1 mg/ml PEG and the antibody response determined fifteen days later. In this experiment the PEG was not covalently attached to the rabbit protein. The results (data not shown) demonstrate no differences in the immunogenicity of any of the samples, and suggest that PEG itself is not an adjuvant.

EXAMPLE V

Figure 5:
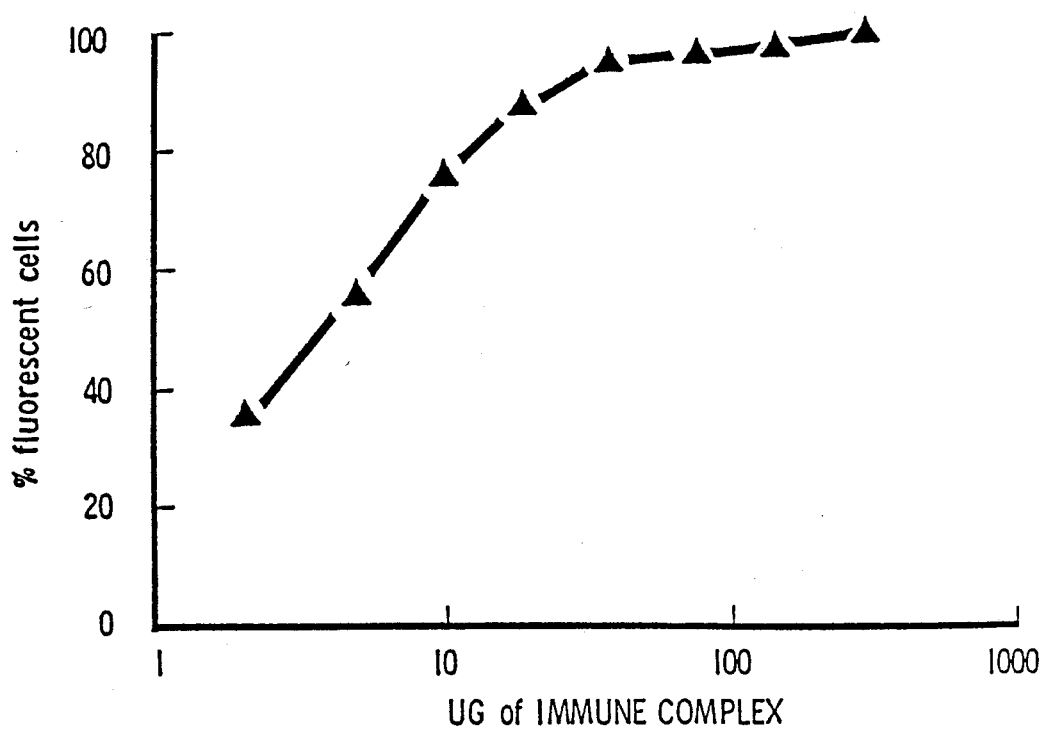
FIG. 5 represents binding of immune complexes to P388.D1 cells. Immune complexes were prepared from rabbit anti-conalbumin and fluorescein-labeled hen egg conalbumin (3 moles conalbumin/mole of antibody). An aliquot from each immune complex of $10^6$ cells was incubated for 30 minutes with the concentration of immune complex shown on the abscissa. The number of fluorescent cells was determined by flow cytometry.

Elimination of Fc receptor binding by mPEG antibody modification according to the invention A. The binding of immune complexes, prepared from rabbit anti-conalbumin antibody and fluorescein-labeled conalbumin to the murine macrophage P388.D1 cell line is shown in FIG. 5. These data show a concentration-dependent binding of the immune complexes to most cells in the population. This binding curve was not significantly altered when immune complexes were prepared using several different antigen to antibody ratios.

Figure 6:
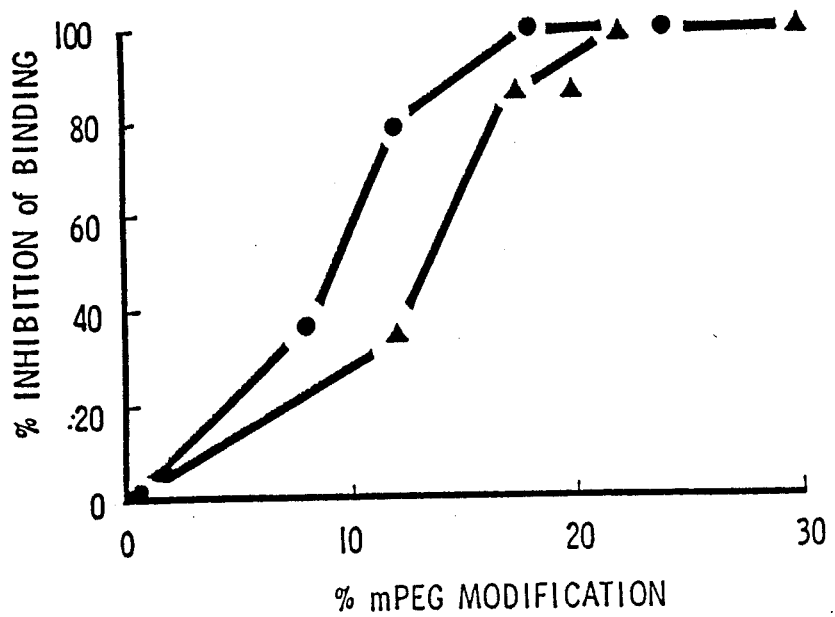
FIG. 6 represents binding of immune complexes prepared using 3 moles of fluorescein-labeled hen egg conalbumin and 1 mole of mPEG-modified rabbit anti-conalbumin to P388.D1 cells. A 40 μg (determined from data in FIG. 5) aliquot of each immune complex was incubated with $10^6$ P388.D1 cell for 30 minutes. The number of fluorescent cells was determined by flow cytometry. The % mPEG modification was established by TNBS amino group analysis. Autofluorescence was observed in 17% of the cells. Different symbols depict experiments performed on different days with different samples of PEG-modified antibody.

To investigate the effect of mPEG-modification on Fc binding, a concentration of immune complexes was chosen from the curve in FIG. 5 to give approximately 75% binding, and this concentration was used in subsequent experiments. Binding experiments, described in FIG. 5, were then repeated with immune complexes prepared using mPEG-modified antibodies according to the invention. The results of a typical experiment, shown in FIG. 6, demonstrate complete inhibition of Fc binding when less than 20% of the amino groups had been mPEG-modified. It should be stressed that the mPEG-modified antibodies used in these experiments all retained 100% of their initial antibody activity as determined in competitive enzyme-linked immunoassays. Repetitions of this experiment using immune complexes prepared from different lots of mPEG-modified antibody, resulted in a similar inhibition of Fc binding. Thus, Fc binding can be totally inhibited when the antibody involved in the immune complex contains 15–20% of its amino groups modified with mPEG in active ester-mediated reaction.

Figure 7:
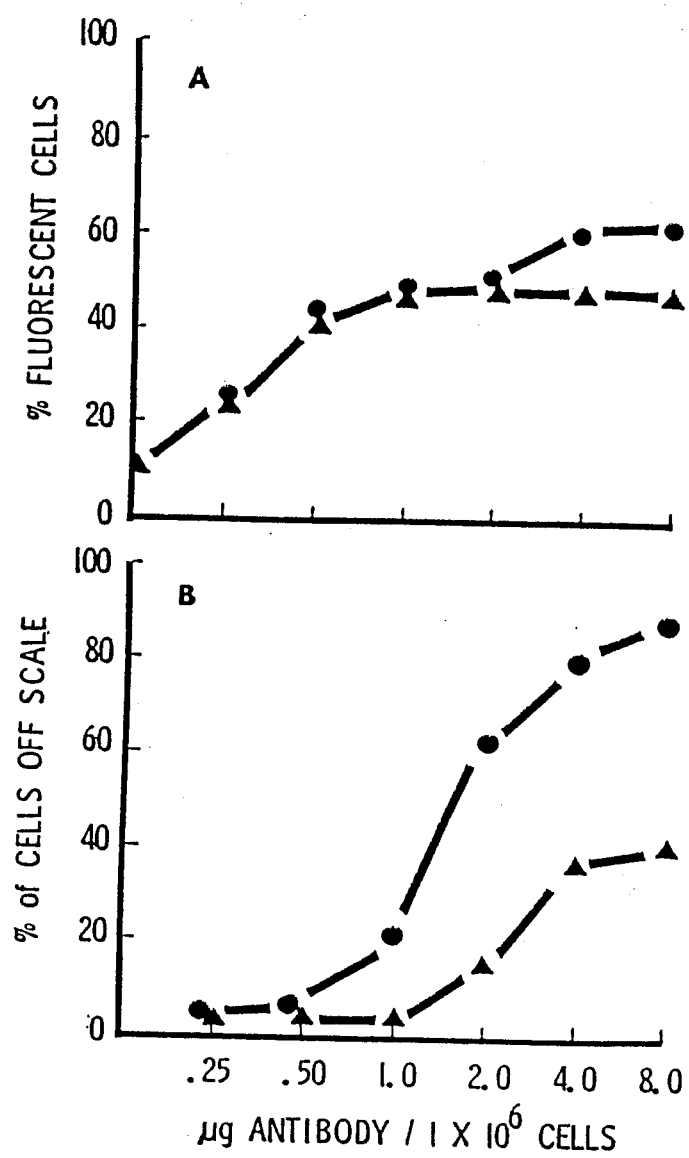
FIG. 7 represents binding of fluorescein-labeled rabbit anti-mouse immunoglobulin (▲) and mPEG-modified fluorescein-labeled affinity purified rabbit anti-mouse immunoglobulin to (●) to $10^6$ mouse splenocytes. Fluorescent cells were determined by flow cytometry. Panel A depicts the number of fluorescent cells as a function of antibody concentration. Panel B reports the number of cells in which fluorescence intensity was off scale on the flow cytometer.

B. To further investigate the effect of mPEG-modification of Fc binding, a sample of fluorescein-modified rabbit anti-mouse immunoglobulin was modified with mPEG according to the invention and binding of this double-modified reagent was tested on mouse splenocytes FIG. 7 compares the titration curves of fluoresceinated rabbit antibody on mouse splenocytes prior to and following mPEG-modification. From this figure it can be seen that both reagents appear to be equally sensitive in detecting mouse B-cells (FIG. 7A). However, using an excess of fluoresceinated reagent, the cells detected by mPEG-modified antibody appear to have an upper limit to the cellular fluorescence intensity whereas cells detected by the reagent that was not mPEG-modified show an increased fluorescence intensity (FIG. 7B).

Figure 8:
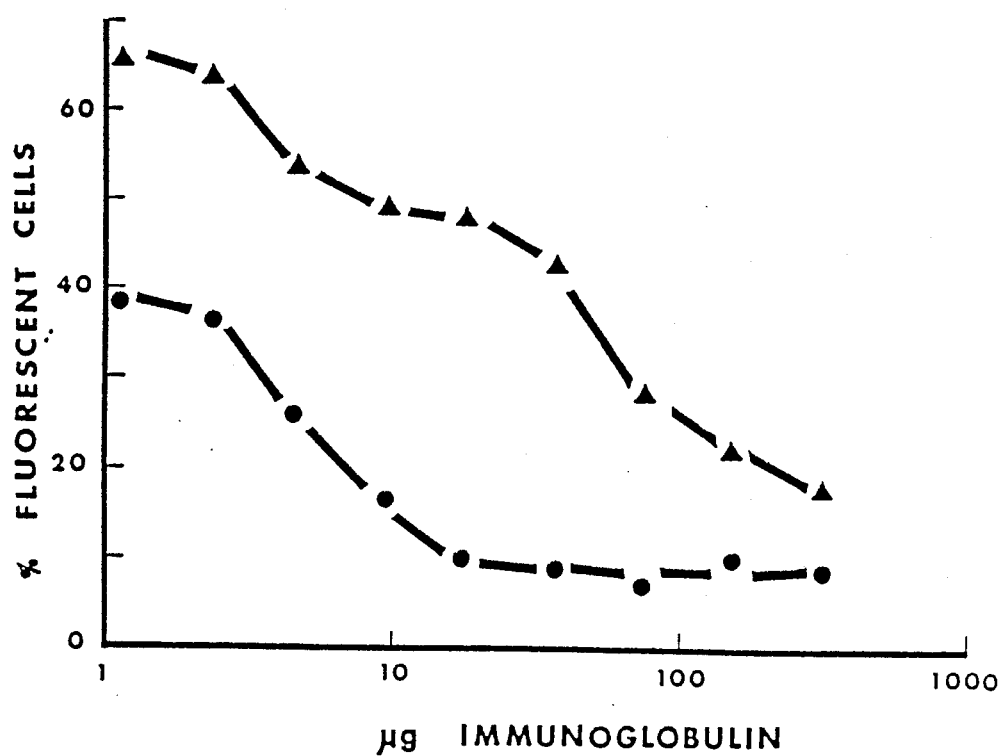
FIG. 8 represents competitive inhibition of the binding of fluorescein-labeled rabbit anti-mouse immunoglobulin to mouse splenocytes. Purified mouse IgG in the amount listed on the abscissa was incubated in the presence of either 8 μg fluorescein-labeled rabbit anti-mouse immunoglobulin (▲) or 8 μg of the same reagent that was also mPEG-modified (●) and $1 \times 10^6$ murine splenocytes. Following washing the cells with PBS, the number of fluorescent cells was determined by flow cytometry. In this experiment, auto-fluorescence was seen in 8% of cells. With no added inhibitor mPEG-modified antibody detected 39% of cells and unmodified antibody 65%.

C. It was demonstrated that the mPEG-modified reagent binds to cell surface immunoglobulin whereas the non mPEG-modified reagent exhibits nonspecific binding to cell surface Fc receptors. To evaluate this finding purified mouse immunoglobulin was used to competitively inhibit the binding of both reagents to mouse splenocytes. The results of this experiment, shown in FIG. 8, clearly demonstrate that the binding of the classical fluoresceinated reagent (not mPEG-modified) could not be completely inhibited by antigen whereas binding of the mPEG-modified reagent was totally inhibited. Furthermore, the amount of mouse immunoglobulin required to competitively inhibit the binding of the mPEG-modified reagent to mouse splenocytes was that concentration that would be predicted to be inhibitable based on theoretical binding calculations.

Figure 9:
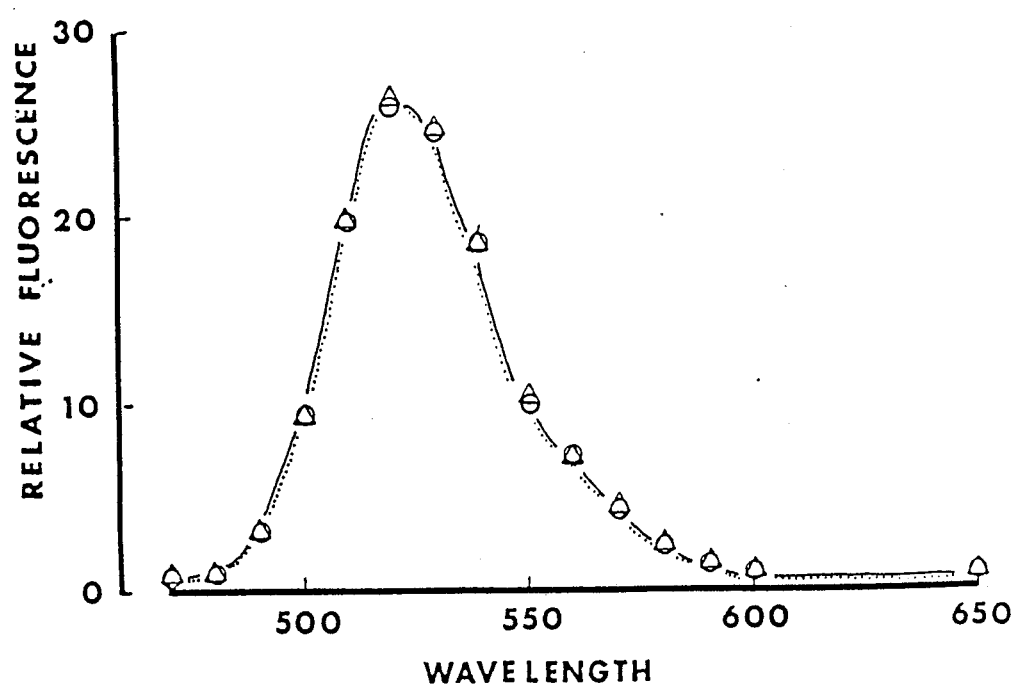
FIG. 9 represents effect of modification on fluorescence emission spectra of mPEG-modified, fluorescein-labeled antibody. An affinity purified rabbit anti-mouse immunoglobulin reagent was modified with FITC to an F/P ratio of 3.7 (M). A fraction of this reagent was modified with mPEG (30% of amino groups modified) and the fluorescence emission spectra of the mPEG-modified (▲) and the unmodified (●) fluorescein-labeled antibody was determined at 0.80 mg/ml in a 0.30 cm cuvette using an AMINCO spectrofluorometer with an excitation wave length of 493 nm.

D. Since under conditions of saturating reagent concentration the cells detected using a classical reagent were brighter than cells detected using the mPEG-modified reagent, the possibility existed that a mPEG-modification might quench fluorescein fluorescence. To test this possibility, the fluorescent emission spectra was determined for the rabbit anti-mouse immunoglobulin reagent prior to and following mPEG-modification. These emission spectra are shown in FIG. 9. No effect of mPEG-modification is observed on either the emission intensity or spectra. These data suggest that at the concentration of mPEG used in the Examples to modify antibody, there is no loss of sensitivity.

RESULTS

PEG-modified antibodies according to the invention exhibit markedly reduced immunogenicity, low specific binding capacity for cell surface Fc receptors, and retention of antigen-binding activity. mPEG modification of antibodies also essentially eliminates Fc receptor binding. Covalent modification of more than 15% of amino groups of rabbit anti-conalbumin antibody with mPEG completely prevented immune complexes prepared with this antibody from binding to the Fc receptor on the murine macrophage cell line, P388.D1. Similar sensitivities are observed for mPEG-modified fluorescein labelled antibodies since mPEG modification does not quench fluorescein fluorescence. A fluorescein labelled rabbit anti-mouse immunoglobulin, when modified with mPEG, exhibited no detectable binding to murine splenocyte Fc receptors by flow cytometry. Thus, mPEG modification is a practical method of eliminating Fc binding for use in cell and tissue staining such as in immunohisto- chemical procedures and flow cytometry. The lack of toxicity of PEG-modified protein in vivo suggests that it will also provide a method for decreasing background tissue binding as well as for reducing immunogenicity in the diagnostic and therapeutic uses of antibodies in humans.

What is claimed is:

1. A PEG-modified antibody obtained by reaction of a carboxylated polyethylene glycol with a carboxyl activating agent to form a polyethylene glycol active ester intermediate, and reaction of the active ester intermediate with an antibody to form the PEG-modified antibody, wherein said PEG-modified antibody is biologically-active, covalently linked to polyethylene glycol, and has decreased immunogenicity, decreased nonspecific reactivity, and increased specific reactivity as compared to unmodified antibody.

2. The PEG-modified antibody of claim 1, wherein the polyethylene glycol is a substituted or unsubstituted polymer having a molecular weight of from about 1000 to 5000.

3. The PEG-modified antibody of claim 1, wherein the polyethylene glycol is monomethoxypolyethylene glycol.

4. A reagent for an immunohistochemical process comprising the PEG-modified antibody of claim 1.

5. The PEG-modified antibody of claim 1, wherein the carboxylated polyethylene glycol reactant is substantially non-immunogenic, and the resulting modified antibody is substantially non-toxic and non-immunogenic.

6. The PEG-modified antibody of claim 1, wherein at least about 10% of the TNBS-available amino groups on the antibody molecule are covalently modified with polyethylene glycol.

7. The PEG-modified antibody of claim 1, wherein the antibody is a monoclonal antibody.

8. The PEG-modified monoclonal antibody of claim 7, wherein the polyethylene glycol is monomethoxypolyethylene glycol.

9. The PEG-modified antibody of claim 1, wherein about 35% of the TNBS-available amino groups are covalently modified with monomethoxypolyethylene glycol.

10. The PEG-modified antibody of claim 9, wherein from about 10% to 20% of the TNBS-available amino groups are covalently modified with monomethoxypolyethylene glycol.

11. The PEG-modified antibody of claim 1, wherein the carboxylated polyethylene glycol is succinylated polyethylene glycol, and the carboxyl activating agent is N-hydroxysuccinimide.

12. The PEG-modified antibody of claim 11, wherein the polyethylene glycol is monomethoxypolyethylene glycol.

13. The PEG-modified antibody of claim 11, wherein the modified antibody is characterized by increased biologic specificity as compared to the unmodified antibody.

14. The PEG-modified antibody of claim 1 complexed with an active moiety.

15. The PEG-modified antibody complex of claim 14, wherein the active moiety is a radionuclide, drug, toxin, or fluorescer.

16. The PEG-modified antibody complex of claim 15, wherein the antibody is an anti-tumor antibody.

17. In an immunological diagnostic method wherein an antibody or complex thereof is employed in an immunoreaction as a diagnostic agent, the improvement comprising employing the PEG-modified antibody of claim 1 or complex thereof as the diagnostic agent.

18. The method of claim 17, wherein the method is a method for diagnosing cancer.

19. The method of claim 17, wherein the PEG-modified antibody or complex thereof is an antibody complexed with a drug, radionuclide, toxin, or fluorescer.

20. The method of claim 17, wherein the diagnostic method comprises administering the PEG-modified antibody or complex thereof to a human.

21. The method of claim 20, wherein the PEG-modified antibody or complex thereof is a heterologous species antibody.

22. A method for inhibiting Fc binding activity of an immunoglobulin comprising covalently modifying the immunoglobulin with polyethylene glycol by reaction of a carboxylated polyethylene glycol with a carboxyl activating agent to form a polyethylene glycol active ester intermediate, and reaction of the ester intermediate with an immunoglobulin to form a biologically-active polyethylene glycol-immunoglobulin derivative.

* * * * *